Figure 1:
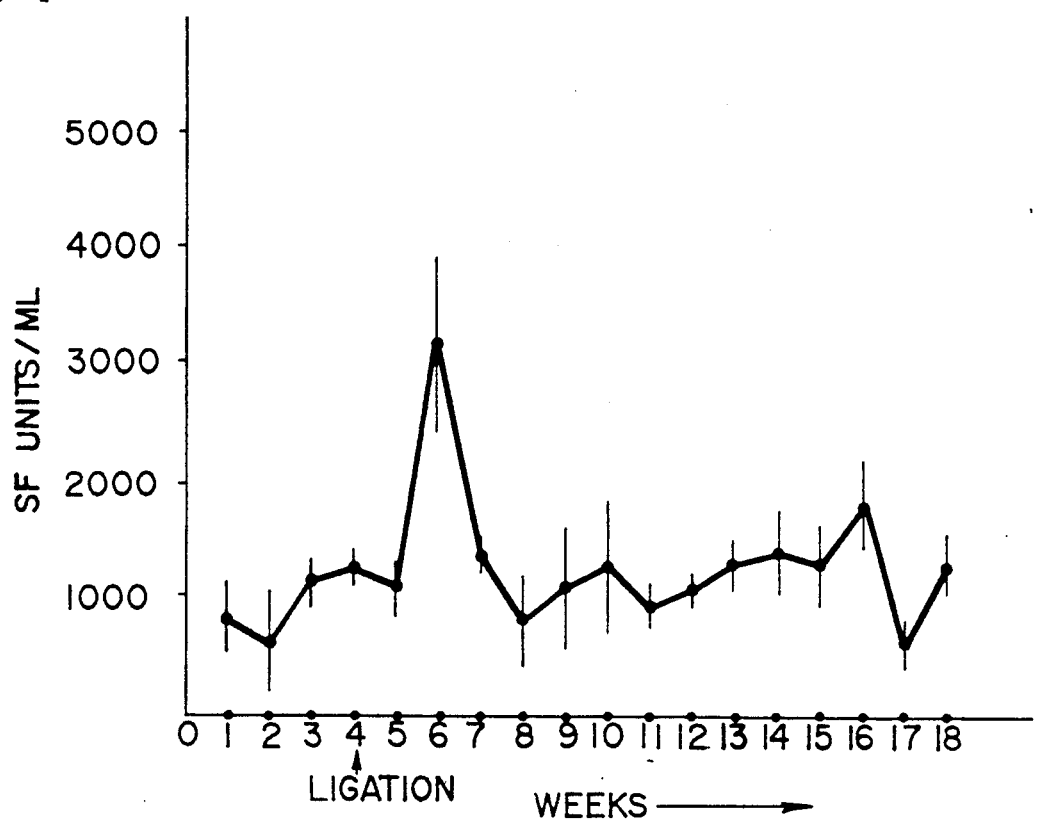
Figure 2A:
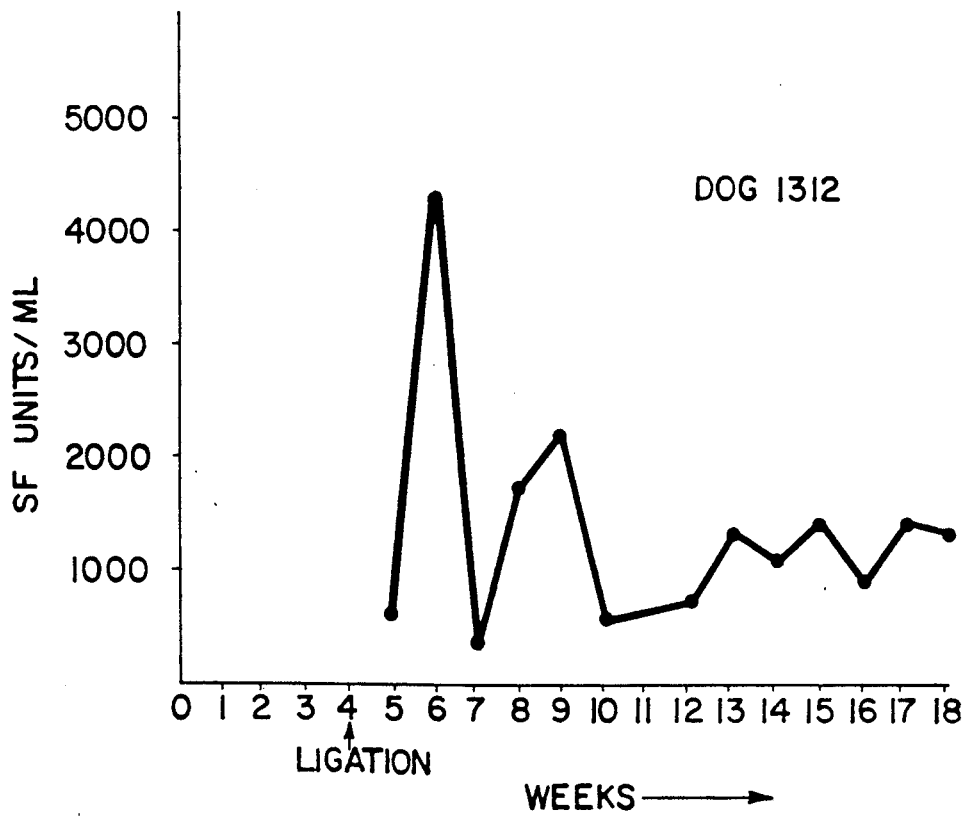
Figure 2B:
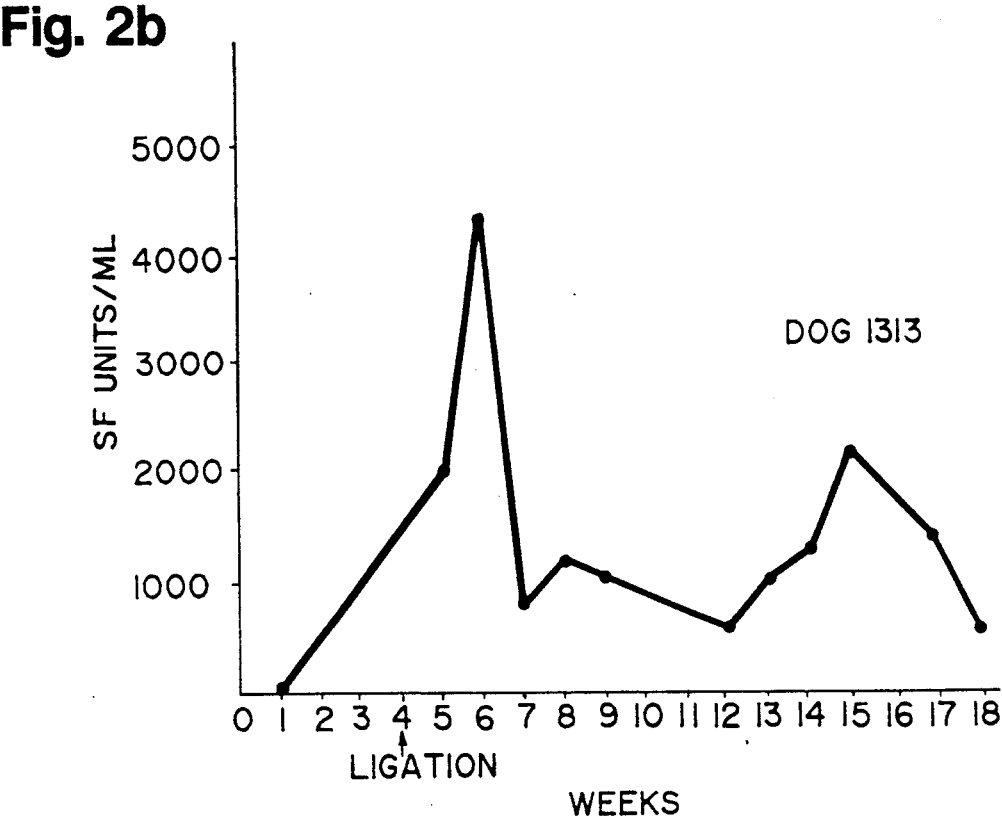
Figure 2C:
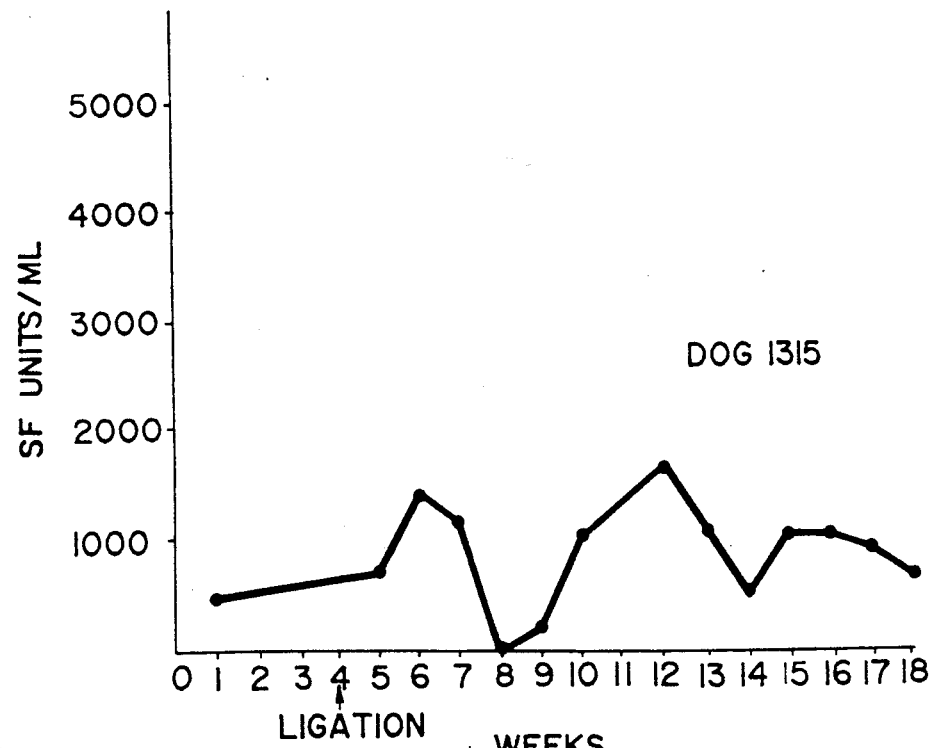
Figure 2D:
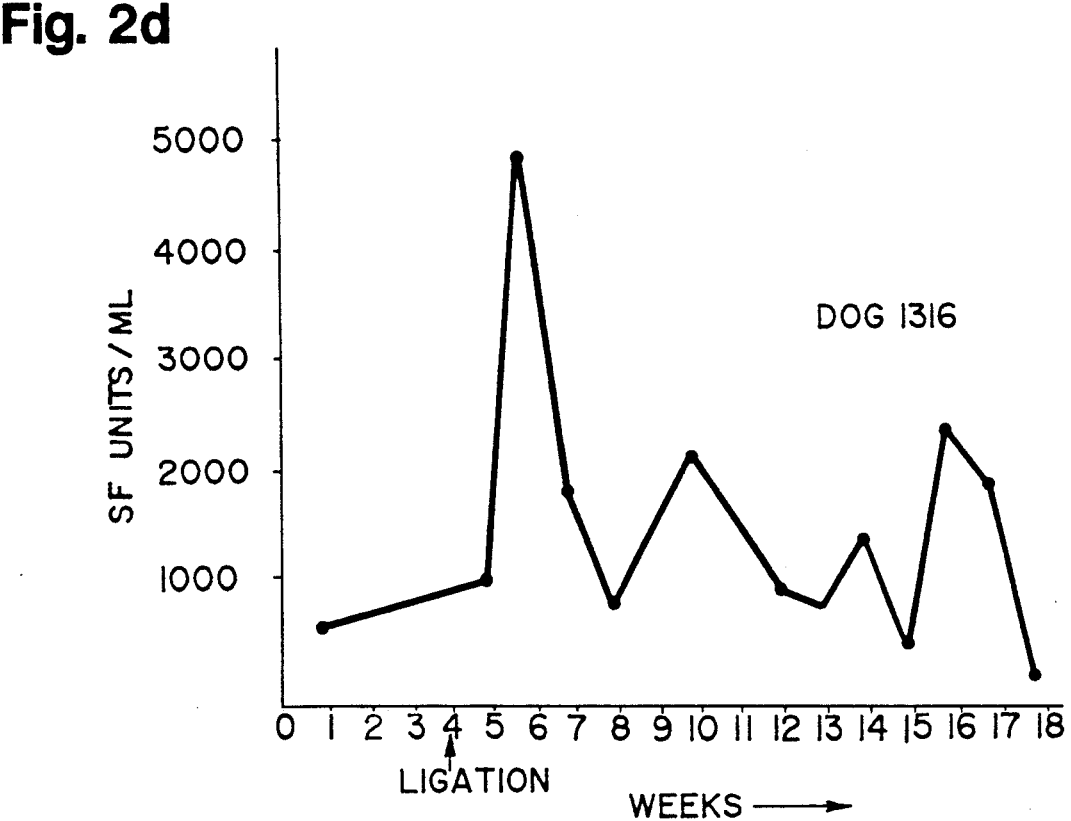
Figure 2E:
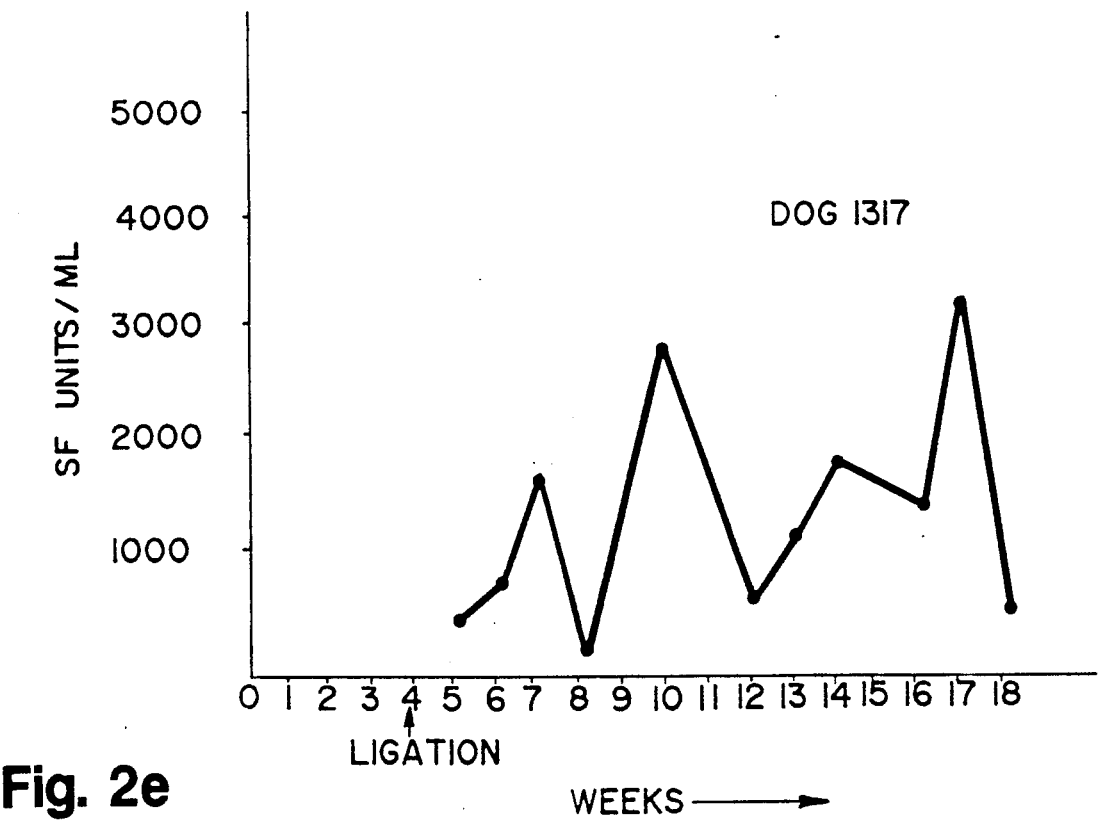

United States Patent [19]

Chambers

[11] Patent Number: 5,041,373
[45] Date of Patent: Aug. 20, 1991

[54] METHOD FOR DETERMINING PERIODONTAL DISEASE

[75] Inventor: Donald A. Chambers, Evanston, Ill.

[73] Assignee: The Board of Trustees of the University of Illinois, Chicago, Ill.

[21] Appl. No.: 317,138

[22] Filed: Mar. 1, 1989

Related U.S. Application Data

[63] Continuation of Ser. No. 96,803, Sep. 10, 1987, abandoned, which is a continuation of Ser. No. 814,065, Dec. 19, 1985, abandoned, which is a continuation of Ser. No. 575,552, Jan. 31, 1984, abandoned.

[51] Int. Cl.$^5$ .................. G01N 33/535; C12Q 1/52; C12Q 1/32
[52] U.S. Cl. .................. 435/7.9; 435/7.1; 435/16; 435/26
[58] Field of Search .................. 435/7.1, 7.9, 16, 26, 435/4, 15, 805, 810; 436/525

[56] References Cited

U.S. PATENT DOCUMENTS

| | | | |
|---|---|---|---|
| 3,458,403 | 7/1969 | Katsunuma | 435/16 |
| 3,546,074 | 12/1970 | Deutsch | 435/16 |
| 3,691,018 | 9/1972 | McNamara et al. | 435/18 |
| 3,723,064 | 3/1973 | Liotta | 436/66 |
| 3,814,669 | 6/1974 | Goldenberg | 435/16 |
| 3,899,397 | 8/1975 | Morin | 435/16 |
| 3,926,564 | 12/1975 | Giaever | 422/57 |
| 3,979,184 | 9/1976 | Giaever | 422/57 |
| 4,012,285 | 3/1977 | Pfleiderer et al. | 435/7.4 |
| 4,042,335 | 8/1977 | Clement | 422/56 |
| 4,054,646 | 10/1977 | Giaever | 424/12 |
| 4,059,407 | 11/1977 | Hochstrasser | 422/56 |
| 4,235,962 | 11/1980 | Sanderson | 435/16 |
| 4,471,055 | 9/1984 | Opp | 436/128 |
| 4,654,310 | 3/1987 | Ly | 436/164 |
| 4,801,535 | 1/1989 | Babler et al. | 435/16 |

FOREIGN PATENT DOCUMENTS

0097904 1/1984 European Pat. Off. .
0158993 10/1985 European Pat. Off. .

OTHER PUBLICATIONS

"Evaluation of the NIDR Periodontal Disease Research Activity", Report of the Ad Hoc Scientific Evaluation Panel to the Director of the National Institute of Dental Research (NIDR), Washington, D.C., Apr. 1976.

"Processings of the Workshop on Quantitative Evaluation of Periodontal Diseases by Physical Measurement Techniques", J. Dent. Res. 58(2):547–553 (1979).

Fluorescence Immunoassay Techniques, in *Immunochemical Techniques*, Langione et al., eds. (Academic Press, 1981), pp. 1–105.

Armitage, in *Biologic Basis on Periodontal Maintenance Therapy* (Praxis Publishing Co., Berkeley, CA, 1980).

Bang et al., Helv. Odont. Acta 16:89–93 (1972).

Bang et al., Archs oral Biol. 15:445–451 (1970).

Barnett et al., J. Dent. Res. 61:IADR Abstr. No. 1260 (1982).

Belanger et al., Clin. Chimica Acta (1973) 48:15–18.

Brown et al., Infection and Immunity 28:82–91 (1980) as cited in Biol. Abstr. 70:46446 (1980).

Bustos et al., J. Dent. Res. 61:IADR Abstr. No. 1261 (1982).

Boldt et al., J. Dent. Res. 61:Abstr. No. 260 (1982).

Chambers et al., J. Periodontol. 55(9):526–530 (1984).

Chung et al., J. Dent. Res. 61:IADR Abstr. No. 1257 (1982).

Cimasoni, *Crevicular Fluid Updated* (S. Karger, New York, 1983).

Clark et al., in *Enzyme–Immunoassay*, Maggio, ed. (CRC Press, Boca Raton, FL, 1980), pp. 167–179.

Ebersole et al., J. Dent. Res. 61:IADR Abstr. No. 1254 (1982).

(List continued on next page.)

Primary Examiner—Esther L. Kepplinger
Assistant Examiner—Toni R. Scheiner
Attorney, Agent, or Firm—Marshall, O'Toole, Gerstein, Murray & Bicknell

[57] ABSTRACT

An objective method for determining the presence of active periodontal disease in mammals, comprising assaying cervicular fluid for the presence of elevated levels of the enzyme aspartate aminotransferase.

30 Claims, 3 Drawing Sheets

OTHER PUBLICATIONS

J. Dent. Res. 61:abstr. 254-262 (1982).
Friedman et al., J. Periodont. 54(6):347-350 (1983).
Friedman et al., J. Dent. Res. 61:IADR Abstr. No. 1259 (1982).
Garvey et al., *Methods in Immunology*, 3rd Ed. (W. A. Benjamin, Inc., Reading, MA, 1977), pp. 7-38, 194-213, 215-270, 524.
Giaever, J. Immunol. (1973) 110(5):1424-1426.
Greenstein et al., J. Periodontol. (1981) 52(8):420-424.
Gronblad, Acta Odontol. Scand. (1982) 40:87-95.
Haffajee et al., J. Clin. Perio. (1983) 10:257-265.
Hausmann et al., Calcif. Tissue Int. (1979) 29:133-139.
Henry et al., Am. J. Clin. Path. 30(9):149-166 (1960).
Hirschfeld et al., J. Periodontol. (1978) 49(5):225-237.
Hunter, in *Immunochemistry*, vol. 1, Weir, ed. (Blackwell Scientific Publications, London, 1973), pp. 14.1-14.25.
Ishikawa, J. Biochem, (1973) 73:1319-1321.
Karkiewicz et al., Rev. Sci. Instrum. (1980) 51(9):1267-1268.
King, *Practical Clinical Enzymology* (D. van Nostrand Company Ltd, Toronto, 1965), pp. 121-138.
Kowashi et al., Arcs oral Biol. 24:645-650 (1979).
Larmas, Acta odont scand. 30:555-573 (1972).
LeBell et al., Archs oral Biol. 23:925-928 (1978).
Lehninger, *Biochemistry*, 2nd ed. (Worth Pub. Co., NY, 1975).
Lin et al., Chem. Abstr. 99:49332t (1983).
Lindhe et al., J. Periodont. Res. (1973) 8:1-10.
Loe et al., Acta Odont. Scand. (1963) 21:533-551.
Maiolini et al., J. Immunol. Methods (1975) 8:223-234.
Morin et al., Clin. Chem. 19(7):776-778 (1973).
Moss, in *Enzymes in Cardiology Diagnosis and Research*, Hearse et al., eds. (John Wiley & Sons, New York, 1979), pp. 145-198.
Nakamura et al., J. Periodontol. 38:134 (1967).
O'Toole et al., J. Dent. Res. 61:IADR Abstr. No. 1258 (1982).
Patters et al., J. Dent. Res. 61:IADR Abstr. No. 1256 (1982).
Podhradsky et al., Archs. oral Biol. 27:615-616 (1982).
Ramfjord, J. Periodontol. (1967) 38:602-609.
Ratnaike et al., Clin. Chim. Acta 74:281-288 (1977).
Rej, Clin. Biochem. 16:17-19 (1983).
Rej et al., Clin. Chem. 19(1):92 (1973).
Rej, Chem. Abstr. 95:20207n (1980).
Rej et al., Chem. Abstr. 100:187773c (1983).
Rej, Clin. Chem. 25(4):555-559 (1979).
Rej, Clin. Chem. 26(12):1694-1700 (1980).
Rej, Clin. Biochem. 12:250-254 (1979).
Sarkisov et al., Chem. Abstr. 92:20207 (1980).
Schenkein et al., J. Periodontol. 48(12):772-777.
Schmidt et al., Clin. Chim. Acta 15:283, 289 (1967).
Schroeder et al., J. Periodontol. (1980) 51(1):6-19.
Silness et al., Acta odont. scand. (1964) 22:9-135.
Smith, in *Enzymes in Cardiology Diagnosis and Research*, Hearse et al., eds. (John Wiley & Sons, New York, 1979), pp. 199-246.
Smith et al., in *Enzymes in Cardiology Diagnosis and Research*, Hearse et al., eds. (John Wiley & Sons, New York, 1979), pp. 133-143.
Smith, in *Enzymes in Cardiology Diagnosis and Research*, Hearse et al., eds. (John Wiley & Sons, New York, 1979), pp. 115-131.
Stovsky et al., J. Dent. Res. 61:IADR Abstract No. 1255 (1982).
Worah et al., Clin Chem. (1980) 26(7):986 (Abstr. #141).
Reitman et al., Amer. J. Clin. Path. (1957) 28:56-63.
Schmid et al., J. Dent. Res. 67:185 (1988).
Yang et al., J. Dent. Res. 61:Abstr. 259 (1982).

METHOD FOR DETERMINING PERIODONTAL DISEASE

This application is a continuation of copending application Ser. No. 096,803, filed 10 Sept. 1987, now abandoned, which in turn is a continuation of application Ser. No. 814,065 filed 19 Dec. 1985, now abandoned, which in turn is a continuation of application Ser. No. 575,552, filed Jan. 31, 1984, now abandoned.

BACKGROUND OF THE INVENTION

The invention pertains to methods of determining the presence of periodontal disease in mammals, and more particularly to methods of determining active periodontal disease by assaying for the presence of elevated levels of the enzyme aspartate aminotransferase.

Periodontal diseases are inflammatory diseases of microbial etiology affecting the supporting tissues of the teeth. These diseases, which affect over 70% of the adult population, are the leading causes of tooth loss in people over 35 years of age. Costs associated with periodontal disease, including cost of treatment and the economic cost due to loss of productivity, are extremely high. It was estimated in 1976 that the cost of effective management of all those suffering from periodontal disease (more than 100 million people) would be many times the 1.5 billion dollars spent at that time [see "Evaluation of NIDR Periodontal Disease Research Activity—Report of the Ad Hoc Scientific Evaluation Panel", National Institutes of Dental Research, Washington, D.C. (April 1976)].

The term "periodontal disease" encompasses two major subclasses of disease, gingivitis and periodontitis. "Gingivitis" is characterized by inflammation of the gums in the absence of bone and attachment loss. See Loe, H. and P. Silness, Acta Odont. Scand. 21:533 (1963). "Periodontitis" is generally accepted to be an advanced stage of gingivitis, further characterized by formation of periodontal pockets between the gum tissue and tooth, followed by loss of bone from the tooth and weakening of tooth attachment, eventually leading to tooth loss. See Ramfjord, S., J. Periodontol. 38:602 (1967). Periodontitis may be further classified, e.g. juvenile periodontitis, local periodontitis, acute necrotizing periodontitis, chronic inflammatory periodontitis (CIPD). CIPD is the most common form of periodontitis among American adults and is characterized by loss of attachment of periodontal ligament to cementum, apical migration of junctional epithelium, and loss of alveolar bone. Both gingivitis and periodontitis are characterized by accumulation of crevicular fluid (a transudate of serum) at the junction of the teeth and gums.

Although periodontal disease is one of the most prevalent bacterial diseases in the civilized world, no objective diagnostic assay is available. In its early stages the disease may be asymptomatic; it is also frequently episodic, with a cyclical pattern of destructive activity interspersed with periods of latency or spontaneous partial regression. Presently available methods of measuring periodontal disease include subjective observational indices such as those of Loe, H. and P. Silness, Acta Odont. Scand. 21:533 (1963) for gingivitis and Ramfjord, S., J. Periodontol. 38:602 (1967) for periodontitis. These indices are based on criteria such as bleeding on gentle probing, pocket depth, attachment loss, and radiographic evidence of bone loss. Unfortunately, these clinical indicators, with the exception of bleeding on probing, are generally acknowledged to be reflective of past disease and prior damage. Of these indicators, only bleeding on probing (bleeding of gum tissue due to probing of the gum line or pocket with a hard instrument, e.g. probe or curet) has been claimed to correlate with active periodontal disease. However, recently the diagnostic value of bleeding on probing has been questioned. See Haffajee, A. D., S. S. Socransky, and J. M. Goodson, J. Clin. Perio. 10:257-265 (1983).

It is a purpose of this invention to provide an objective assay for the determination of the presence of active periodontal disease.

It is further a purpose to provide an objective assay for the presence of active periodontal disease, which assay is rapid, simple, and non-invasive.

It is another purpose of this invention to provide a kit for an objective assay to determine the presence of active periodontal disease, for use by clinicians.

It is yet another purpose of this invention to provide a kit for a simple, rapid, objective assay to determine the presence of active periodontal disease, for home use by the patient.

DESCRIPTION OF THE INVENTION

It has now been discovered that the presence of elevated levels of the enzyme aspartate aminotransferase in crevicular fluid is highly correlative of the presence of active periodontal disease. The presence of elevated levels of this enzyme in crevicular fluid is also predictive of a high probability of progressive, as opposed to non-progressive, periodontal disease and corresponding tissue damage.

The enzyme aspartate aminotranferase [EC 2.6.1.1; L-aspartate:2-oxoglutarate aminotransferase] (previously known as glutamic aspartic transaminase, glutamic aspartic aminotransferase, glutamic aspartic aminopherase, glutamic oxalacetic transaminase, GOT, G.O.T., or GO-T) (hereinafter referred to as AST) catalyzes the reaction:

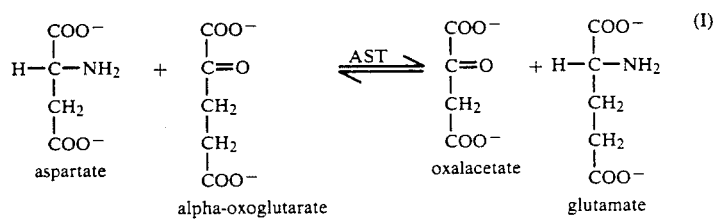

$$\text{aspartate} + \text{alpha-oxoglutarate} \xrightleftharpoons{AST} \text{oxalacetate} + \text{glutamate} \quad (I)$$

Pyridoxal phosphate is required as a prosthetic group. The enzyme also catalyzes other reactions (e.g. beta-sulphinyl pyruvate to L-cysteinesulphonate and beta-sulphonyl pyruvate to L-cysteate) but at a much slower rate.

AST is found in both the mitochondria and cytosol of eukaryotic cells. The mitochondrial and extramitochondrial forms of pig-heart AST differ in their physical and chemical characteristics and amino acid composition. Both forms have a molecular weight of about 90,000 daltons and consist of 2 approximately equal size subunits. AST is involved in a variety of catabolic and anabolic pathways for amino acids. See Lehninger, A. L., *Biochemistry*, 2nd ed. (Worth Publishers, New York, 1975).

AST has been found in detectable levels in plasma, bile, cerebrospinal fluid, saliva, and gum [see e.g. J. King, *Practical Clinical Enzymology* (D. Van Nostrand Co., Ltd., Toronto, 1965), pp. 122]. Increased levels of blood serum AST have been correlated with acute myocardial infarction, pulmonary embolism, acute pancreatitis, viral and toxic hepatitis, active cirrhosis, obstructive jaundice, muscular dystrophy, acute dermatomyositis, polymyositis, and paroxysmal myoglobinuria. Increased levels of AST in cerebrospinal fluid has been reported in glioblastoma, stroke, and idiopathic epilepsy seizures. See King, supra, pp. 135–136. However, the fact that elevated levels of AST in crevicular fluid correlate with the presence of active periodontal disease was not known prior to this invention. This correlation was first shown in two abstracts presented at the American Association for Dental Research Meetings, Cincinnati, Ohio, March 17–20, 1983 (Crawford, J. M., S. Mukherjee, D. A. Chambers, and R. Cohen, Abstract No. 241, and Mukherjee, S., J. Crawford, D. A. Chambers, and R. Cohen, Abstract No. 242, both published on or after Feb. 1, 1983).

By "elevated level of AST" is meant an amount of AST substantially in excess of the level of AST normally found in the blood serum of healthy adults of the species being tested. The normal human adult range of serum AST is 5–18 milli-International Units (m-I.U.) when assayed by Procedure I below; when assayed by Procedure II below the normal human adult serum AST range is 4–15 m-I.U. (assayed at 25° C.), 6–23.5 m-I.U. (assayed at 32° C.), 8.5–32 m-I.U. (assayed at 37° C.). See King, supra, p. 134. One milli-International Unit is defined as the amount of AST which will convert 1 nanomole ($10^{-9}$ mole) of substrate per minute.

The crevicular fluid may be collected by any suitable means, e.g. by means of a microsyringe with a fine (preferably blunt) needle or a capillary tube (preferably calibrated), or by means of an absorbent strip of filter paper or fabric, e.g. endodontic paper points or Whatman filter paper (W & R Balston, Ltd., England). The sample is collected by direct contact of the sampling means with crevicular fluid at the interface of the gum and the tooth. The amount of sample is determined by calibration of the collection means, or alternatively by subsequent measurement. The amount of fluid on a filter paper strip may be determined by means of a galvanometer, e.g. a Periotron (Harco Electronics Ltd., Winnipeg, Canada). The collected sample may be stored at −20 to 4° C. for periods of up to 24 hours before assaying.

The presence (or absence) of AST in the collected sample of crevicular fluid is determined by any suitable means, e.g. by colorimetric or immunological assay. By "colorimetric assay" is meant an assay in which the presence or absence of the test compound is determined directly or indirectly by observing the appearance or disappearance of a compound which absorbs visible, infrared, or ultraviolet light. The absorption of light may be observed directly or via instrumentation such as a spectrophotometer. By "immunological assay" is meant an assay which depends on the reaction of specific antibodies with the test compound; the formation of antigen-antibody complex is detected by means of a suitable label, e.g. radioactivity, fluorescence, free radicals, bacteriophages, or enzyme-labelling.

Colorimetric Assays

A variety of commercially available assays are known for the enzyme AST. The known colorimetric assays follow one of two reaction schemes, each of which couples the AST-catalyzed production of oxalacetate (Reaction I above) with further subsequent, easily measured reaction(s):

Procedure A(1) (see King, supra, pp. 130–132)

The production of oxalacetate by Reaction I is coupled with the formation of a 2,4-dinitrophenylhydrazone-derivative, which has a reddish-brown color and absorbs light at 520 nm:

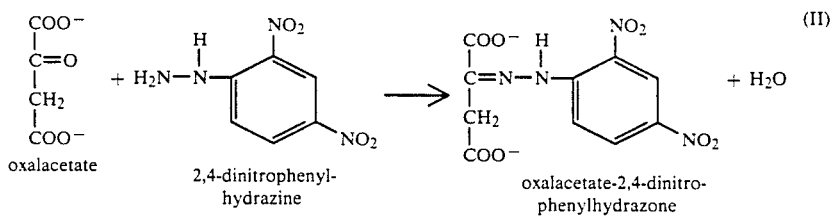

(II)

The test sample is combined with excess L-aspartic acid and alpha-oxoglutaric acid (enzyme substrates) and incubated for a fixed period of time to allow AST present in the sample to convert the substrates to oxalacetate and glutamate. Excess 2,4-dinitrophenylhydrazine is then added; the reaction mixture is then further incubated for a fixed period to allow conversion of the oxalacetate to its 2,4-dinitrophenylhydrazone derivative. The color of the 2,4-dinitrophenylhydrazone derivative is brought out by addition of excess alkali and the color, once stabilized, is read directly by the unaided eye or by recording the absorption of light at 520 nm on a spectrophotometer. If a spectrophotometer is used, the blank contains all reagents except the sample. The results may be quantified by comparison with a standard color or absorbance chart, prepared by analyzing a series of samples containing known amounts of AST. In this procedure, all reagents are added in excess relative to AST, therefore the amount of AST is the rate-limiting factor.

Procedure A(2) (see King, supra, pp. 130–132)

This is a variation of procedure A(1) above, wherein the oxalacetate produced by Reaction (I) is not directly added to the 2,4-dinitrophenylhydrazine but rather is first converted to pyruvate, which in turn is converted to the pyruvate—2,4-dinitrophenylhydrazone derivative:

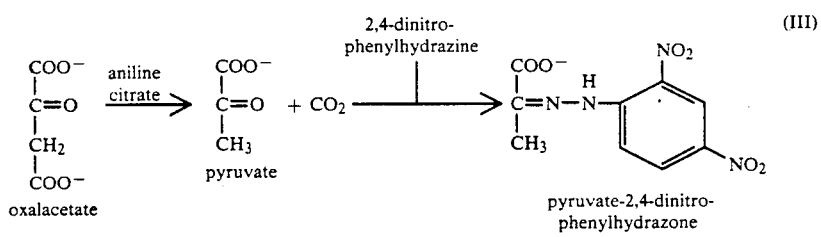

The excess aniline citrate is added after incubation of the sample with the substrate and before addition of the 2,4-dinitrophenylhydrazine reagent. The remainder of the procedure follows that of A(1) above.

Procedure B (see King, supra, pp. 127-129; Henry, R. J., N. Chiamori, O. J. Golub, and S. Berkman, Am. J. Clin. Path. 30(9): 149-166 (1960))

In this assay the oxalacetate produced by Reaction (I) is the substrate in a second reaction, in which malate dehydrogenase converts oxalacetate to malate. Malate dehydrogenase requires nicotine adenine dinucleotide, reduced form (NADH) as a coenzyme:

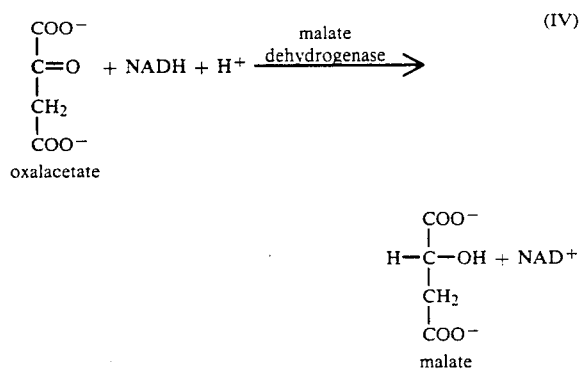

NADH absorbs ultraviolet light at 340 nm, whereas oxalacetate, malate, and the oxidized form of nicotine adenine dinucleotide (NAD+) do not. Therefore the rate of conversion of oxalacetate to malate can be followed by monitoring the rate of disappearance of NADH at 340 nm. In a system in which all reagents except AST are in excess, the amount of AST is rate-limiting for the coupled reactions (I) and (IV) and is directly proportional to the rate of disappearance of the NADH.

All steps are performed at one temperature, preferably at a temperature selected from the range of about 18-40° C. Buffer, aspartate, sample, malate dehydrogenase, and NADH are combined and incubated until the readings at 340 nm are stable. )This preincubation period allows time for endogenous pyruvate to be converted to lactate by endogenous lactate dehydrogenase. This reaction also requires coenzyme NADH and if allowed to proceed concurrently with the malate dehydrogenase reaction would introduce an artificially high rate of disappearance for NADH. If desired, sufficient lactate dehydrogenase may be added to the preincubation mixture to insure complete conversion of any pyruvate present. This may also allow the preincubation period to be shortened or eliminated entirely.) The blank contains all reagents except aspartate. Once this initial incubation is complete, the transamination reaction (I) is started by addition of alpha-oxalacetate. The rate of disappearance of NADH is monitored at 340 nm over a period of time and recorded. This rate is converted to milli-International Units (m-I.U.) by the equation:

$$m\text{-}I.U. = (\Delta A_{340}/\text{min})(1000)\left(\frac{Y}{6.2}\right)\left(\frac{1}{Z}\right)(T_f)$$

wherein $\Delta A_{340}/\text{min}$ is the change in absorbance at 340 nm per minute, Y is the total reaction volume in milliliters, Z is the volume of sample in milliliters, 6.2 is the micromolar extinction coefficient for NADH, and $T_f$ is a temperature conversion factor based on the temperature at which the assay was run:

| Reaction Temperature (°C.) | Temperature Conversion Factor | | |
|---|---|---|---|
| | 25° C. | 32° C. | 37° C. |
| 18 | 1.62 | 2.5 | 3.35 |
| 19 | 1.5 | 2.34 | 3.14 |
| 20 | 1.39 | 2.18 | 2.94 |
| 21 | 1.3 | 2.04 | 2.75 |
| 22 | 1.22 | 1.9 | 2.58 |
| 23 | 1.14 | 1.78 | 2.41 |
| 24 | 1.07 | 1.67 | 2.26 |
| 25 | 1.00 | 1.56 | 2.12 |
| 26 | 0.94 | 1.46 | 1.98 |
| 27 | 0.88 | 1.37 | 1.86 |
| 28 | 0.825 | 1.28 | 1.74 |
| 29 | 0.774 | 1.2 | 1.64 |
| 30 | 0.726 | 1.13 | 1.54 |
| 31 | 0.68 | 1.06 | 1.44 |
| 32 | 0.64 | 1.00 | 1.36 |
| 33 | 0.6 | 0.94 | 1.28 |
| 34 | 0.567 | 0.885 | 1.2 |
| 35 | 0.53 | 0.83 | 1.13 |
| 36 | 0.5 | 0.78 | 1.06 |
| 37 | 0.47 | 0.735 | 1.00 |
| 38 | 0.445 | 0.695 | 0.94 |
| 39 | 0.42 | 0.655 | 0.89 |
| 40 | 0.395 | 0.617 | 0.84 |

Since the rate of these enzyme reactions is temperature-dependent, care must be taken so that any comparison of assay results is done only on data corrected for temperature variance. In using this assay for diagnosis of periodontal disease, the practitioner is advised to select one reference temperature (e.g. 25, 32, or 37° C.) and to consistently convert all results to the equivalent at this temperature. Alternatively, the practitioner may choose to run all assays at one particular temperature, preferably selected from the range of 18-40° C.; in this case all of the practitioner's data can be directly compared but correction for temperature may be necessary before comparison can be made with the results of other practitioners or with published data.

The disappearance of the fluorescent NADH may also be observed by the unaided eye under ultraviolet (340 nm wavelength) light.

Examples of commercially available AST assays using Procedure B are A-gent ™ Aspartate Aminotransferase Assay (Abbott Cat. No. ABA-50, ABA-100, Abbott-VP, Abbott Laboratories, Chicago, IL), and Worthington Statzyme ® GOT (Worthington Cat. No. CGOT, Worthington Diagnostic Systems, Inc., Freehold, N.J.).

Immunological Assays

Immunological assays are based on the reaction of the test substance (antigen) with an antibody specific for that substance; when the antibody is present in excess the formation of an antigen/antibody complex is directly proportional to the amount of antigen present. The antigen/antibody complex may be precipitated, collected, and measured; alternatively, the antibody may be labelled with a marker which is easily detected; the antigen/antibody complex is thus also labelled. Removal of excess unreacted antibody leaves only the antigen/antibody complex as labelled and the amount of label is directly proportional to the amount of complex, and thus to the amount of antigen, present. Accordingly, the presence of AST in crevicular fluid may be assayed by reaction of test sample with AST-specific antibodies.

Antibodies are obtained according to procedures well known to those skilled in the art, by immunizing a suitable host animal with AST and subsequently purifying the resultant antibodies from host serum. See, e.g. *Methods in Immunology*, 3rd Ed. (J.S. Garvey, N. E. Cremer, and D. H. Sussdorf, eds.) (W. A. Benjamin, Inc., Reading, MA (1979), pp. 7-38, 218-270.

The antigen/antibody complex formed by reaction of AST with AST-specific antibodies may be precipitated by ammonium or sodium sulfate. See, e.g., *Methods in Immunology*, 3rd Ed. (J. S. Garvey, N. E. Cremer, and D. H. Sussdorf, eds.) (W. A. Benjamin, Inc., Reading, MA (1979), pp. 218-270. If desired, the precipitate is collected by suitable means, e.g. centrifugation or filtration, and quantified. Rej, R., C. R. Keese, and I. Giaever, Clin. Chem. 27(9):1597-1601 (1981) describe a simple visual immunoassay for AST based on indium precipitation of AST/anti-AST antibody complex An indium-coated glass slide is spotted with purified known AST. A known amount of anti-AST antibody is then added in the presence of test sample. The AST in the test sample competes with the AST on the plate for the limited number of antibody binding sites available; a high concentration of AST in the sample will bind most of the antibody binding sites and little antibody will be available to bind to the AST on the plate. Conversely, if only a small amount of AST is present in the sample, a larger amount of antibody will be free to bind to the AST on the plate. After allowing time for this equilibrium to become established, excess antibody is washed from the slide. The assay is based on the principle that scattering of electromagnetic radiation due to small particles is strongly influenced by coating the particles with thin dielectric layers. The scattering of light through the glass slide by the particles of indium metal is increased by absorption of dielectric proteins, e.g. AST and AST/anti-AST antibody complex Single and multiple layers of protein can be distinguished by the amount of scatter; the more layers the more scatter and the darker the spot. The results can be quantified by densitometry. Thus, a high concentration of sample AST will inhibit anti-AST antibody binding to the AST on the plate and the resulting spot will be relatively light; a low concentration of AST in the test sample will permit more anti-AST antibody binding to the AST on the plate and the resulting spot will be relatively darker. The results may be quantified by comparison with a standard curve.

Alternatively and preferably, the AST or anti-AST antibody is labelled with an easily detectable marker The formation of AST/anti-AST antibody complex is determined directly by measuring the marker, or indirectly by measuring competitive inhibition with a known amount of pure AST. Examples of suitable markers are radioactive isotopes! fluorophores, ferritin, free radicals, bacteriophages, or enzymes. Radioisotopes, fluorophores, and enzymes are preferred. Examples of suitable radioactive isotopes are, e.g., $^{125}I$, $^{131}I$, $^{14}C$, $^{35}S$, and $^{3}H$. For a summary of immunoassay techniques using radioactive labels (radioimmunoassays), see Hunter, W. M. in *Handbook of Experimental Immunology*, 2nd Ed. (D. M. Weir, ed.) (Blackwell Scientific, Oxford, 1973), pp. 14.1-14.25, incorporated herein by reference. Examples of suitable fluorescent labels are, e.g., fluorescein isothiocyanate, 4-methylumbelliferone, beta-galactosylumbelliferone, and 7-beta-galactosylcoumarin-3-carboxamido]hexylamine. For a summary of immunoassay techniques using fluorophore labels (fluoroimmunoassays), see Fluorescence Immunoassay Methods in *Immunochemical Techniques*, J.L. Langone and H. VanVunakis, eds. (Academic Press, 1981), pp. 1-105 Worah, D.N., K. K. Yeung, F. F. Ward, and R. J. Carrico, Clin. Chem. 26:986 (1980); Ishikawa, E., J. Biochem. 73:1319 (1973); Ngo, T. T., R. J. Carrico, R. C. Boguslaski, and J. F. Burd, J. Immunol. Meth. 42:93 (1981), all incorporated herein by reference. AST/anti-AST antibody complexes may also be labelled by reaction with a labelled second antibody, which is specific for the (first) anti-AST antibody For example, if the (first) anti-AST antibody is of mouse origin, it will act as an antigen for a second antibody of, e.g., goat origin which is specific for mouse IgG. Reaction of the AST-/mouse anti-AST antibody complex with labelled goat anti-mouse IgG antibody will form a further complex, AST/mouse anti-AST antibody/goat anti-mouse IgG antibody which will also be labelled For a summary of immunoassay techniques utilizing enzyme labels (enzyme immunoassays and enzyme-linked immunosorbent assays), see Clark, B. R., and E. Engwall, in *Enzyme-Immunoassay*, E. T. Maggio, ed. (CRC Press, Boca Raton, Florida, 1980), pp. 167-179, incorporated herein by reference. See also Ebersole, J. L., E. A. Adamson, M. A. Taubman, and D. J. Smith, J. Dent. Res. 61:318 (Abstr. No. 1254) (1982) [use of alkaline phosphatase-labelled rabbit anti-human IgG antibodies to measure antibodies to periodontopathic bacteria in crevicular fluid].

The present invention further comprises a kit for the rapid, simple determination of the presence of periodontal disease by assaying for elevated levels of aspartate amino transferase in crevicular fluid, said kit comprising 1) means for collecting a sample of crevicular fluid, and 2) one or more compositions of matter suitable for the assay of AST. Preferably, said kit comprises 1) an absorbent filter strip, 2) a reaction vessel, 3) premeasured amounts of L-aspartic acid and alpha-oxoglutarate, combined in one package, 4) a premeasured amount of buffer, preferably phosphate buffer, at a suitable pH, 5) a premeasured amount of 2,4-dinitrophenylhydrazine, 6) a premeasured amount of alkali, preferably sodium hydroxide, and 7) a standardized color chart The sample is collected by absorption on the filter strip, which is then placed in the vial. The reconstituted L-aspartic acid and alpha-oxoglutarate are added, along with the buffer, to the reaction mixture, mixed, and incubated to allow formation of oxalacetate and glutamate. The 2,4-dinitrophenylhydrazine is then added and the reaction mixture is further incubated to allow formation of oxalacetate-2,4-dinitrophenylhydrazone. Finally the alkali is added and the color is allowed to stabilize. Comparison with the standard chart provides a determination of the amount of AST present; amounts in excess of those found in the serum of normal adults is indicative of active, progressive periodontal disease. This kit is suitable for in-home use by patients as well as office use by clinicians.

A further understanding of the Invention can be had from the following non-limiting Examples. As used hereinabove and below unless expressly stated to the contrary, all temperatures and temperature ranges are expressed in degrees Centigrade (°C.), and the term ambient or room temperature refers to about 20° C. The term percent or (%) refers to weight percent and the term moles(s) refers to gram mole(s). The organic acids described hereinabove and below are known to form salts with various bases; it is to be understood that for the purposes of this invention the salt and free acid forms of these organic acids are equivalent.

EXAMPLE 1

2,4-Dinitrophenylhydrazine Assay (method of King, supra, pp. 130–132)

Reagents:

(a) 0.1 M phosphate buffer, pH 7.4 [Mix 840 ml 0.1 M disodium hydrogen phosphate (17.8 g $Na_2HPO_4.2H_2O$ per liter) and 160 ml 0.1 M potassium dihydrogen phosphate (13.609 g $KH_2PO_4$ per liter). Add a few drops of chloroform to prevent bacterial growth.]
(b) substrate solution [Dissolve 2.66 g D,L-aspartic acid and 30 mg alpha-oxoglutaric acid in 20.5 ml 1 N sodium hydroxide with the aid of gentle heat. Transfer quantitatively to a 100 ml flask, wash in, and make to the mark with buffer solution. Add a drop of chloroform and store at 4° C.]
(c) color reagent [Dissolve 200 mg 2,4-dinitrophenylhydrazine in hot 1 N hydrochloric acid and make to 1 liter with 1 N HCl. Store in brown bottle. A precipitate may form after a few weeks, but the reagent is suitable for use for periods of up to 3 months. Precipitation is not retarded by storage in the refrigerator.]
(d) 0.4 N sodium hydroxide
(e) 2 mM oxalacetate standard [Dissolve 26.8 mg oxalacetic acid in 100 ml 0.1 M phosphate buffer, pH 7.4. Prepare immediately before use.]

Procedure

Into each of two tubes labelled "test" and "blank", pipette 1 ml of substrate solution and allow to attain bath temperature of 37° C. Add 0.2 ml crevicular fluid to the "test" and mix gently by shaking. Incubate both tubes at 37° C. for 30 min. Without removing the tubes from the water bath, add 1 ml color reagent to each tube and incubate for further 20 min. Remove the tubes from the bath; add 10 ml 0.4 N sodium hydroxide and mix by inversion. After the initial rapid fading of color (1 minute), record optical density using a green filter or transmitted light at 520 nm. Translate the optical density into milli-International Units (m-I.U.) using the standard curve. Specimens with activity in excess of 50 m-I.U. should be deleted and the assay repeated.

Standard Curve

Set up tubes as indicated (reagent amounts given in mls):

|  | Tube # | | | | | | |
| --- | --- | --- | --- | --- | --- | --- | --- |
|  | 1 | 2 | 3 | 4 | 5 | 6 | 7 |
| substrate solution | 1.0 | 0.95 | 0.9 | 0.85 | 0.8 | 0.75 | 0.7 |
| 2 mM oxalacetate standard | 0 | 0.05 | 0.1 | 0.15 | 0.2 | 0.25 | 0.3 |
| 0.1 M phosphate buffer, pH 7.4 | 0.2 | 0.2 | 0.2 | 0.2 | 0.2 | 0.2 | 0.2 |
| Activity in m-I.U. | Blank | 8.3 | 16.7 | 25 | 33.3 | 41.7 | 50.0 |

Incubate at 37° C. for 30 min. Add 1 ml color reagent to each tube and continue incubation for a further 20 min. Remove tubes from water bath, add 10 ml 0.4 N sodium hydroxide to each tube, and record optical densities. Plot the optical densities against the activities shown to give the standard curve.

EXAMPLE 2

2,4-Dinitrophenylhydrazine Assay (method of King, supra, pp. 130–132)

Reagents (a) 0.1 M phosphate buffer, pH 7.4
(b) substrate solution
(c) aniline citrate reagent [Mix equal parts of redistilled aniline and a solution of 50 g citric acid in 50 ml water. Make mixture fresh at least weekly.]
(d) color reagent
(e) 0.4 N sodium hydroxide
(f) 2 nM pyruvate standard [Dissolve 22 mg sodium pyruvate in 100 ml buffer solution Use the same day as prepared.]

The 0.1 M phosphate buffer, substrate solution, color reagent, and 0.4 N sodium hydroxide are prepared as in Example 1.

Procedure

Into each of two tubes labelled "test" and "blank", pipette 1 ml of substrate solution and allow to attain bath temperature of 37° C. Add 0.2 ml crevicular fluid to the "test" and mix by gentle shaking. Exactly 60 minutes after adding the serum, and without removing from the water bath, add 0.05 ml aniline citrate reagent to both tubes, and 0.2 ml serum to the "blank" tube. Mix well and allow a minimum of 5 minutes to complete decarboxylation. Add 1 ml of color reagent to each tube and leave in the water bath for a further 15 minutes. Remove the tubes from the water bath; add 10 ml 0.4 N sodium hydroxide, and mix by inversion. After the initial rapid fading of color (1 min), record the optical density using a green filter or transmitted light at 520 nm. Transfer the optical density in activity units from the standard curve. Specimens with activity much in excess of 50 m-I.U. should be diluted and the assay repeated.

Standard Curve:

Set up tubes as indicated (reagent amounts given in mls):

|  | Tube # | | | | | | |
| --- | --- | --- | --- | --- | --- | --- | --- |
|  | 1 | 2 | 3 | 4 | 5 | 6 | 7 |
| substrate solution | 1.0 | 0.95 | 0.9 | 0.85 | 0.8 | 0.75 | 0.7 |
| 2 mM pyruvate standard | 0 | 0.05 | 0.1 | 0.15 | 0.2 | 0.25 | 0.3 |
| 0.1 M phosphate buffer, pH 7.4 | 0.2 | 0.2 | 0.2 | 0.2 | 0.2 | 0.2 | 0.2 |
| Activity in m-I.U. | Blank | 8.3 | 16.7 | 25 | 33.3 | 41.7 | 50.0 |

The same procedure is followed as for the standard curve in Example 1.

EXAMPLE 3

2,4-Dinitrophenylhydrazine Assay (Cat. No. 505, Sigma Chemical Co., St. Louis, MO)

Reagents (a) Sigma Prepared Substrate, Stock No. 505-1 [0.2 M D,L-aspartic acid, 1.8 mM alpha-ketoglutaric acid, phosphate buffer pH 7.5 at 25° C.]
(b) Sigma Color Reagent, Stock No. 505-2 [approximately 0.02% 2,4-dinitrophenylhydrazine in 1 N HCl]
(c) 0.4 N sodium hydroxide
(d) Calibration Standard Solution, Stock No. 505-10 [1.5 mM sodium pyruvate]

Blank

To test tube add 1.0 ml Sigma Prepared Substrate and 1.0 ml Sigma Color Reagent Add 0.2 ml crevicular fluid and incubate 20 min at 25±5° C. Add 10.0 ml 0.4 N sodium hydroxide, wait 5 min.

Test

To a test tube add 1.0 ml Sigma Prepared Substrate; place in 37° C. water bath to warm. Add 0.2 ml crevicular fluid; shake gently to mix; incubate at 37° C. for 60 min.

Add 1.0 ml Sigma Color Reagent; shake gently and leave at 25±5° C. After 20 min, add 10.0 ml 0.4 N sodium hydroxide solution; mix by inversion.

After 5 min, read optical density (O. D.) against blank prepared as above; the wavelength of transmitted light must be the same as that used for the standard curve. Activity is determined in Sigma-Frankel Units (SFU) from the standard curve (1 SFU will form $4.82 \times 10^{-4}$ micromoles glutamate per minute at pH 7.5 and 25° C.) (1 I. U. = 0.48 SFU).

Standard Curve

Set up tubes as indicated in columns 2, 3, and 4:

| Tube No. | Calibration Standard Solution (ml) | Sigma Prepared Substrate (ml) | Water | AST Activity (SFU/ml) | O.D. |
| --- | --- | --- | --- | --- | --- |
| 1 | 0 | 1.0 | 0.2 | 0 | Blank |
| 2 | 0.1 | 0.9 | 0.2 | 20 |  |
| 3 | 0.2 | 0.8 | 0.2 | 55 |  |
| 4 | 0.3 | 0.7 | 0.2 | 95 |  |
| 5 | 0.4 | 0.6 | 0.2 | 148 |  |
| 6 | 0.5 | 0.5 | 0.2 | 216 |  |

Add 1.0 ml Sigma Color Reagent to each tube. Shake gently and incubate at 25±5° C. After 20 min, add 20.0 ml 0.4 N sodium hydroxide to each tube. Mix by inversion and wait at least 5 min. Read and record optical density of tubes 2–6, using tube #1 as a reference blank. The wavelength of transmitted light is selected from the range 490–520 nm. The AST activity values given above have been corrected for the difference in temperature between the test assay (37° C.) and the standard curve assay (25±5° C.).

EXAMPLE 4 1

NADH assay (see King, supra, pp. 127–129)

Reagents (a) 0.1 M phosphate buffer, pH 7.4 [Mix 840 ml 0.1 M disodium hydrogen phosphate (17.8 g $Na_2HPO_4 \cdot 2H_2O$ per liter) and 160 ml 0.1 M potassium dihydrogen phosphate (13.609 g $KH_2PO_4$ per liter). Preserve by adding a few drops of chloroform.]
(b) 0.2 M aspartate solution [Dissolve 2.66 g L-aspartic acid in 20 ml 1 N sodium hydroxide with the aid of gentle heat. Cool and make to 100 ml with buffer. Add a drop of chloroform and store at 4° C.]
(c) 0.1 M alpha-oxoglutarate solution [Dissolve 1.47 g alpha-oxoglutaric acid in 20 ml 1 N sodium hydroxide and make to 100 ml with buffer. Store at 4° C.]
(d) malate dehydrogenase [Dilute with buffer to 500 μg/ml or 1000 units/ml. The enzyme is unstable diluted, therefore prepare small amounts as needed.]
(e) NADH solution, 1 mg/ml buffer. [Keep frozen when not in use, or better prepare only as required.]
(f) stock dichromate solution [29 mg $K_2Cr_2O_7$ with a few drops of concentrated sulfuric acid per 100 ml water. Dilute as required for zero reference.]

Procedure

Into 2 cuvettes pipette the following reactants:
1) Test
  1.3 ml 0.1 M phosphate buffer, pH 7.4
  1.0 ml 0.2 M aspartate solution
  0.2 ml crevicular fluid
  0.1 ml malate dehydrogenase
  0.2 ml NADH solution
2) Control
  2.3 ml 0.1 M phosphate buffer, pH 7.4
  0.2 ml crevicular fluid
  0.1 ml malate dehydrogenase
  0.2 ml NADH solution
and against a suitable zero reference, follow the reduction of endogenous oxo-acids by recording optical density at 340 nm until two consecutive readings are the same. If the optical density falls to a low value add a further 0.1 ml of enzyme and continue to monitor the reaction. When this preliminary incubation is complete, record the temperature of the cuvette compartment, and if further NADH is not required add 0.1 ml buffer to both cuvettes. The transamination reaction is initiated by adding 0.2 ml 0.1 M alpha-oxoglutarate solution and mixing well with the aid of a thin glass rod. Optical density is now recorded at 1- or 2-minute intervals for at least 10 minutes. The period over which the decrease in optical density is constant with time is used to calculate the enzyme activity:

$$m\text{-}I.U. = (\Delta OD/\text{min}) (1000) \left(\frac{3.1}{6.2}\right)\left(\frac{1}{0.2}\right)(T_f)$$
$$= (\Delta OD/\text{min}) (2500) (T_f)$$

wherein 3.1 is the total reaction volume, 0.2 is the sample volume, 6.2 is the micromolar extinction coefficient of NADH, and $T_f$ is the temperature correction factor given above under "Colorimetric Assays, Procedure B".

EXAMPLE 5

NADH Assay (Method of Henry, R. J., N. Chiamori, 0. J. Golub, and S. Berkman, Am. J. Clin. Path. 30(9):149–166 (1960))

Reagents (a) 1 M phosphate buffer, pH 7.4 [136 g $KH_2PO_4$ plus 33 g NaOH per liter]
(b) 0.1 M phosphate buffer, pH 7.4 [Diluted from 1 M buffer]
(c) NADH solution [2.5 mg/ml 0.1 M phosphate buffer. Can be used for 1 week if kept frozen.]
(d) 0.1 M alpha-ketoglutarate solution, in 0.1 M phosphate buffer [To approximately 35 ml of distilled water in a beaker add 5 ml 1 M phosphate buffer and 0.73 g alpha-ketoglutaric acid. Adjust to pH 7.4±0.1 with 1 N NaOH (approximately 8.1 ml are required). Diluted to 50 ml with water Solution is stable in the refrigerator.]
(e) malate dehydrogenase (MDH) solution [Dilute stock solution with 0.1 M phosphate buffer to yield 10,000 units/ml. This dilute solution should be prepared daily.]
(f) 0.375 M L-aspartate, in 0.1 M phosphate buffer [Dissolve 5.0 g L-aspartic acid in a 250-ml beaker containing approximately 50 ml water and 35 ml 1 N NaOH by mixing and warming on a steam bath (crushing large crystals will help speed solution). Cool to room temperature and add 10 ml of the 1 M phosphate buffer. Adjust to pH 7.4±0.1 with 1 N NaOH, using a pH meter. Dilute to 100 ml with water.]

Procedure

To a cuvet add 1.3 ml 0.1 M phosphate buffer, 1.0 ml 0.375 M aspartate solution, and 0.2 ml crevicular fluid from a thin capillary pipet. Mix and incubate for approximately 30 min in the spectrophotometer or in a water bath at 32° C. Toward the end of this period the absorbance at 340 nm ($A_{340}$) should be measured against a reference solution of $K_2Cr_2O_7$ and then measured again a few minutes later. The 2 readings should check, indicating that the side reaction has ended. If the second reading is lower than the first, readings must be continued until no further change in $A_{340}$ is observed. Furthermore, if the $A_{340}$ is not approximately 0.5, the $K_2Cr_2O_7$ solution should be replaced with one that gives such a reading. (One of the following concentrations of $K_2Cr_2O_7$, containing a few drops of sulfuric acid per 100 ml, will generally be suitable: $2.5 \times 10^{-4}$ M, $1.87 \times 10^{-4}$ M, $1.25 \times 10^{-4}$ M, or $6.25 \times 10^{-5}$ M.) Once the $A_{340}$ has stabilized, add 0.2 ml of 0.1 M alpha-ketoglutarate which has been kept at the temperature of the reaction and mix. Readings of $A_{340}$ should be made every minute for at least 10 min. If the rate is too fast ($\Delta A > 0.075$ per min), the test should be re-run on a dilution of the test sample with buffer The $\Delta A$ per min for each reading should be calculated and those early readings in the lag phase discarded. The later values that seem to be in a steady state within experimental error should be averaged.

$$GOT \text{ units} = \left(\frac{\Delta A \text{ for } t \text{ min}}{t}\right)\left(\frac{1}{\text{ml crevicular fluid used in test}}\right)(1000)$$

It is recommended that the test be run at 32° C. or, if not, the results be corrected to this temperature.

EXAMPLE 6

NADH Assay (Worthington Diagnostic Systems, Inc., Freehold, N.J.)

Reagents

Worthington Statzyme ® GOT, which when reconstituted according to the package insert contains the following:

134.0 mM L-aspartate
6.64 mM 2-oxoglutarate
0.24 mM NADH
5 $\mu$/ml lactate dehydrogenase
1.25 $\mu$/ml malate dehydrogenase
50 mM sodium phosphate buffer, pH 7.4

Procedure

Adjust spectrophotometer to 340 nm and 25° C. Pipette 2.9 ml Statzyme reagent into cuvette and place in spectrophotometer. Incubate for 3–4 min to reach temperature equilibrium and establish blank rate, if any. At zero time, add 0.1 ml of crevicular fluid and record the decrease in $A_{340}$ for 4–5 min. Calculate $\Delta A_{340}$/min from the initial linear portion of the curve.

Standard Curve

Dissolve AST at a concentration of one mg/ml in 0.1 M potassium phosphate pH 7.4. Prepare a series of dilutions to give concentrations of 0.05, 0.10, 0.15, 0.20, and 0.25 $\mu$/ml in 0.1 M phosphate buffer. Assay each dilution by the procedure above. Convert $\Delta A_{340}$/min for each dilution to units/mg by the formula:

$$\text{Units/mg} = \frac{\Delta A_{340}/\text{min}}{(6.2) \text{ (mg enzyme/ml reaction mixture)}}$$

One unit oxidizes one micromole of NADH/min at 25° C. and pH 7.4 under the above-specified conditions.

This standard curve may be used to convert $\Delta A_{340}$/min to units/mg for the test sample.

EXAMPLE 7

NADH Assay (Abbott Laboratories, Chicago, IL)

Reagents

Abbott A-gent ™ SGOT, which when reconstituted according to the package insert contains the following
lactate dehydrogenase, 200 U/liter
malate dehydrogenase, 66 U/liter
L-aspartate, K, 97 mmole/liter of Reaction Mixture
NADH, $Na_2$, 0.28 mmole/liter of Reaction Mixture
alpha-ketoglutarate, Na, 6 mmole/liter of Reaction Mixture
$Na_2HPO_4$, 100 mmole/liter of Reaction Mixture
$KH_2PO_4$, 15 mmole/liter of Reaction Mixture Procedure Aliquot a 3.0 ml portion of reconstituted Abbott A-gent ™ SGOT into a clean, dry test tube and bring the solution to 37° C. by incubation for 3-5 min. Zero the spectrophotometer during the incubation. Without delay add 0.2 ml crevicular fluid, mix, transfer to cuvette and return to 37° C. incubator. (Start timer immediately before addition of crevicular fluid). At exactly 3 minutes, read absorbance and return cuvettes to incubator. (This step should be accomplished within 15 seconds.) Record 3 minute reading. Repeat reading at exactly 11 minutes and record.

If the crevicular fluid is turbid or highly icteric, or if the initial (3 minute) absorbance is below 0.6, the test sample should be diluted and the assay repeated. If the initial absorbance is very high (above 1.0), the instrument should be zeroed against a dichromate solution (see Example 4) or against a tube of A-gent SGOT diluted to an absorbance of about 0.3.

If the spectrophotometer employed can utilize less than 3.0 ml volumes, reagent and crevicular fluid volumes may be decreased proportionally without changing the method of calculation (for example, 0.3 ml of reagent plus 0.02 ml crevicular fluid).

EXAMPLE 8

Indium Immunoassay (see Rej. R. , C. R. Keese, and I. Giaever, Clin. Chem. 27(9): 1597-1601 (1981))

Reagents (a) Buffer A [100 mM Tris, 50 mM NaCl, 1 g/L BSA, 10 mg/L human IgG]
(b) Buffer B [100 mM Tris, 50 mM NaCl]
(c) crevicular fluid, diluted 4- to 16-fold in Buffer A
(d) anti-human-AST antisera, diluted 1,000- to 10,000-fold in Buffer A
(e) indium metal
(f) glass slide
(g) pure AST antigen (0.1 g/L in saline or distilled water)

Procedure

Indium metal is condensed on standard square cover glasses in a reduced-pressure evaporator, by the method of Giaever, L., J. Immunol. 110:1424–1426 (1973). Before use, each slide is cut into four approximately equal squares. Absorbance of the indium slides is determined with a densitometer constructed according to the design of Karkiewicz, L. M., J. A. Panitz, and G. L. Fowler, Rev. Sci. Instrum. 51:1267–1268 (1980).

The crevicular fluid specimen is diluted with an appropriate volume of Buffer A in a 9-ml vial, and diluted anti-human-AST antiserum is added to a total volume of 1.2 ml. This vial is preincubated at room temperature for 1 hour.

The indium slide, prepared as above, is spotted with one small droplet (<5 μl) of pure AST antigen on the indium-coated surface. The slide is incubated for 15 min in a moist chamber, and the unabsorbed antigen is washed gently from the slide with a stream of tap water. The slide is then placed immediately, without drying, in the preincubated solution of crevicular fluid and anti-human-AST antiserum.

After 1.0-hour incubation with gentle shaking at room temperature, the slide is removed from the vial and briefly dipped into a solution of Buffer B, pH 7.5. The buffer is drained off the slide onto filter paper; care must be taken not to touch the surface. The slide is stored in a moist chamber to prevent the surface from drying. Presence of AST in the crevicular fluid is indicated by a darkening of the spot relative to the spot produced by pure AST alone. The more AST in the crevicular fluid, the less antibody will bind to the AST on the slide, and the less darkening is produced. Conversely, the less AST in the crevicular fluid, the more antibody is free to bind to the AST on the slide, and the more pronounced the darkening. The effect may be quantified by densitometry. The absorbance of white light for each spot is determined by comparing the intensity of light transmitted through the spot ($I_s$) with that transmitted through the background immediately adjacent to the spot ($I_b$). The absorbance (A) is calculated at $-\log (I_s/I_b)$.

The darkening may be intensified by addition of about 50 μl of anti-rabbit IgG (diluted 20-fold in Buffer B). After 30 minutes the slide is rinsed gently in running water and dried with compressed air.

Standard Curve

The standard curve is prepared by the above assay, except that the crevicular fluid is replaced with known concentrations of purified AST diluted in Buffer A. The resulting absorbances are plotted against their respective known AST concentrations.

EXAMPLE 9

Radioimmunoassay (RIA)

(See Gronblad, E. A., Acta Odontol. Scand. 40:87 (1982))

Reagents (a) AST (Worthington Diagnostic Systems, Inc., Freehold, NJ)
(b) $^{125}$I-labelled AST in 1% bovine serum albumin [see Hunter, W. M., in *Handbook of Experimental Immunology*, 3rd Ed. (D. M. Weir, ed.) (Blackwell Scientific, Oxford), Ch. 14. $^{125}$I is available from, e.g., New England Nuclear Co., Boston, MA]
(c) anti-AST antibody (IgG fraction) [*Methods in Immunology*, 3rd Ed. (J. S. Garvey, N. E. Cremer, and D. H. Sussdorf, eds.) (W. A. Benjamin, Inc., Reading, MA (1979), pp. 194–215; Rej, R., Clin. Chem. 26 (12): 1694–1700 (1980); Rej, R., Clin. Biochem. 12:250–254 (1979)]
(d) 0.15 M NaCl (e) Solution A [0.15 M NaCl containing 5% bovine serum albumin and 0.02% sodium azide]
(f) phosphate-buffered saline, pH 7.4, containing 0.5% gelatin and 0.1% sodium azide; see *Methods in Immunology*, 3rd Ed., supra, p. 524]

Procedure

Polystyrene tubes (10×70 mm) are coated with antibodies to AST (approximately 0.3 ml of suitably diluted antibodies per tube) and incubated overnight at 4° C. Each tube is washed twice with 1.5 ml of 0.15 M NaCl and then with 0.5 ml Solution A. The tubes are again incubated overnight at 4° C. and washed twice with 0.15 M NaCl and 0.1 ml of various dilutions of crevicular fluid is added, one sample per tube. All dilutions are made in Buffer B. Then 0.3 ml of $^{125}$I-labelled AST in 1% bovine serum albumin, containing approximately 30,000 cpm, is added to each tube. After overnight incubation at 22° C. the tubes are washed twice with 0.15 M NaCl and counted in a gamma counter. The inhibition of binding by AST in the sample is plotted on semi-logarithmic paper and compared with inhibition by known concentrations of AST prepared as a standard curve.

Standard Curve

The above assay is performed using various known concentrations of AST standard in place of the crevicular fluid sample. Results are plotted on semi-logarithmic paper as a function of known AST concentration.

[N. B. The sensitivity of RIA assays are in general dictated by the avidity of the antibodies used.]

EXAMPLE 10

Fluorimetric Immunoassay (See Ngo, T. T., R. J. Carrico, R. C. Boguslaski, and J. F. Burd, J. Immunol. Meth. 42:93 (1981))

Reagents (a) AST see Example 9]
(b) Buffer A [50 mM N, N-bis[2-hydroxyethyl]-glycine buffer, pH 8.2, containing 0.1% sodium azide]
(c) antibody to AST see Example 9]
(d) GUAH-labelled AST
(e) beta-galactosidase [Worthington Biochemical Co., Freehold, N. J.]

Theory

The principle of substrate-linked fluoroimmunoassay is as follows: a fluorigenic enzyme substrate (in this assay, 6-[7-beta-galactosylcoumarin-3-carboxamido]-hexylamine, known as "GUAH") is covalently linked to AST to form a stable protein-substrate conjugate. When beta-galactosidase is added to this conjugate, the galactose residue is hydrolyzed and the fluorescence emission at 450 nm (with excitation at 400 nm) is greatly enhanced. The hydrolysis is inhibited when antibody specific for AST is bound to the labelled AST.

In competitive binding immunoassays wherein labelled and unlabelled (sample) AST compete for binding sites on a fixed amount of anti-AST antibody present, antibody-conjugated labelled AST will be inhibited. Thus the amount of fluorescence measured on free labelled AST will be directly proportional to the amount of unlabelled AST in the sample.

Synthesis of GUAH-labelled AST

Synthesis of GUAH 15 mM 1,6-hexanediamine at pH 9.0 is added to 5 mmole 7-beta-galactosylcoumarin-3-carboxylic acid prepared by the method of Burd et. al. (1977) and adjusted to pH 5.0. At 4° C. 1.16 g (6.15 mmole) of 1-ethyl-3[3-dimethylaminopropyl]carbodiimide (Pierce Chem. Co., Rockford, IL) is added and allowed to react 2 hours at 4° C., then 2 hours at room temperature. 18 mls $H_2O$ and 0.6 g of the carbodiimide are added and allowed to react overnight with the pH maintained at 5.0. The mixture is diluted to 6 liters with $H_2O$ and applied to a CM-Sepharose C-1 column (Pharmacia Fine Chemicals, Piscataway, NJ). After washing with distilled $H_2O$, 1 mM ammonium bicarbonate, and 2 mM ammonium bicarbonate, a linear gradient is applied, generated with 2 mM ammonium bicarbonate and 300 mM ammonium bicarbonate. The absorbance of the eluate is monitored at 280 nm and selected fractions are examined by TLC on Silica Gel-60 plates (Merck & Co., Darmstadt, W. Ger.) using a 0.3 M triethylammonium bicarbonate buffer, pH 7.8: ethanol [3:7] solvent. Fluorescent fractions were pooled and evaporated to dryness, then redissolved in $H_2O$.

Coupling of GUAH with AST 10 mgs dimethyladipimidate dihydrochloride (Pierce Chemical Co., Rockford, IL) and 40 μl triethylamine are added to 8.5 mgs GUAH in 2 ml distilled $H_2O$. After stirring at room temperature for 10 min, 40 mgs AST in 1 ml 0.1 M sodium pyrophosphate buffer, pH 8.5 is added. After stirring at room temperature for 2 hours, the mixture is chromatographed on a 3×50 cm Sephadex G-25 column (Pharmacia Fine Chemicals, Piscataway, NJ) equilibrated with 0.1 M sodium phosphate buffer pH 7.0. Fractions with a higher absorbance at 280 nm than at 340 nm contain labelled protein and are pooled.

The labelled protein is dialyzed extensively at 4° C. against 0.1 M sodium phosphate buffer, pH 7.0, then against the same buffer containing 1 M NaCl, then again by buffer alone, before use. Immediately before use, the labelled protein is diluted to an appropriate concentration with Buffer A. The amount of GUAH incorporated into the AST is calculated from optical absorption data using a calculated extinction coefficient (1 mg/ml, 278 nm) for purified AST and an extinction coefficient (1 mM, 340 nm) of 20.5 for GUAH.

Assay Procedure

Standards are prepared by serial dilution of purified AST. Crevicular fluid samples are diluted in Buffer A.

The immunoassays are conducted in plastic cuvettes (Evergreen Scientific, Los Angeles, (A) by first reacting anti-AST antibody with crevicular fluid and GUAH-labelled AST, followed by enzymatic hydrolysis with beta-galactosidase, as follows:

GUAH-labelled AST in 3.1 ml Buffer A is added to a series of cuvettes, followed by addition of 100 μl of appropriately diluted AST standard or crevicular fluid. 100 μl of anti-AST antibody diluted in buffer A is added to each cuvette and mixed. Enzymatic hydrolysis is initiated by the addition of 100 μl of beta-galactosidase (0.005 U in Buffer A) to successive cuvettes at 30 sec intervals. The reaction is allowed to proceed at room temperature for 30 min and then the fluorescence for successive cuvettes is determined at 30-sec intervals at 450 nm emitted light (400 nm excitation). [NOTE: Absorption at 340 nm diminishes concurrently as absorption at 450 increases.]

Standard Curve

The standard curve is made by plotting fluorescence at 450 nm versus AST concentrations for the standards.

EXAMPLE 11

Enzyme-linked Immunosorbent Assay (ELISA)

(See Maiolini, R., and R. Maseyess, J. Immunol. Methods 8:223 (1975); Belanger, L., C. Sylvestre, and D. DuFour, Clin. Chim. Acta 48:15 (1973); Ebersole, J. L., E. A. Adamson, M. A. Taubman, D. J. Smith, J. Dent. Res. 61:318 (1982))

Reagents (a) PBS [phosphate-buffered saline, pH 7.4; see *Methods in Immunology*, 3rd Ed. (J. S. Garvey, N. E. Cremer, and D. H. Sussdorf, eds.) (W. A. Benjamin, Inc., Reading, MA (1979), p. 524]
(b) PBS-azide [phosphate-buffered saline, pH 7.4, containing 0.02% sodium azide]
(c) Buffer B [0.15 M NaCl, pH 7.4, containing 0.05% Tween-20TM(polyoxyethylene sorbitan monolaurate, available from Fisher Scientific, Fair Lawn, NJ)
(d) alkaline phosphatase-conjugated antibodies to AST [Arrameas, S., T. Ternynck, J-L. Guesdon, Scand. J. Immunol. 8 [suppl.7]:7 (1978)]
(e) Sigma phosphatase substrate [Cat. No. 104, Sigma Chemical Co., St. Louis, MO) [1 mg/ml p-nitrophenylphosphate, 1 mM magnesium chloride, 0.05 M sodium carbonate, pH 9.8]
(f) 1 M sodium hydroxide
(g) AST (Worthington Biochemical Co., Freehold, NJ)
(h) antibody to AST (IgG fraction) [*Methods in Immunology*, 3rd. Ed, supra, pp. 194, 215; Rej, R., Clin. Chem. 26 (12):1694–1700 (1980); Rej, R., Clin. Biochem. 12:250–254 (1979)]

Procedure

Antibody to AST is incubated in polystyrene microtiter plates overnight at 4° C. to allow the antibodies to adsorb to the microtiter plates. The plates are washed 5 times with PBS to remove excess antibodies and then incubated with samples of crevicular fluid diluted in PBS-azide for 2 hours at room temperature on a rotator. This allows any AST present in the crevicular fluid to bind to the anti-AST antibody on the plates at a first antigenic site. The plates are further washed (three times for 5 min with Buffer B) to remove the extraneous components of the crevicular fluid and then incubated with alkaline phosphatase-conjugated antibodies to AST for 16–18 hrs. at room temperature. These labelled antibodies will bind to the AST at a second antigenic site, thus forming a labelled anti-AST antibody/AST-/anti-AST antibody "sandwich" immobilized on the plate.

Sigma phosphatase substrate is added; the p-nitrophenylphosphate is converted by the alkaline phosphatase present on the labelled antibodies to p-nitrophenol, which absorbs light at 400 nm. The reaction is terminated at 30 min by addition of 1 M sodium hydroxide and the presence of p-nitrophenol is measured spectrophotometrically at 400 nm. The amount of p-nitrophenol produced is directly proportional to the amount of alkaline phosphatase present, which in turn is directly proportional to the amount of labelled anti-AST antibody which is directly proportional to the amount of AST present in the crevicular fluid sample.

The quantification of AST in the crevicular fluid samples is determined by reference to a standard curve.

Standard Curve

The above procedure is performed using known concentrations of AST standard in place of the crevicular fluid samples.

Conditions described in this assay are exemplary only. Antibody concentration, buffer pH, length of incubation, etc., can be varied by procedures well-known to those skilled in this art.

EXAMPLE 12

Determination of Periodontal Disease in Beagle Dogs

Five two-year old, male beagle dogs were examined to determine their periodontal health. All dogs showed heavy deposits of plaque and calculus, gingival inflammation and pockets of 1–4 mm in depth. The teeth were scaled and polished, daily brushing was instituted and the animals were maintained on a hard diet. Three weeks later, clinical and histological examination revealed normal gingivae. Biopsy specimens, taken from the upper molar regions of each dog, showed minimal numbers of inflammatory cells in the gingival connective tissue. On day 0, daily brushing was stopped and the dogs were placed on a soft diet (Purina Dog Chow, softened with water) to induce gingivitis. At weekly intervals, blood samples were obtained, crevicular fluid samples were collected from premolar teeth and clinical indices were recorded. Four weeks after induction of gingivitis, periodontitis was induced by placing dental floss ligatures subgingivally around the premolar teeth in the upper right quadrant. Mesial and distal subgingival grooves were prepared on each tooth to keep the ligatures from moving coronally or apically. Collection of blood and crevicular fluid samples and recording of clinical indices were continued for fourteen weeks after ligation. Animals were anesthetized with Surital (thiamylal sodium; Park Davis, N.J.) for collection of samples and recording of clinical indices.

The following clinical parameters were recorded at weekly intervals from day 0 until termination of the study: the plaque index [Silness, P., and H. Loe, Acta Odont. Scand. 22:121 (1964)], gingival index [Loe, H., and P. Silness, Acta Odont. Scand. 21:533 (1963)], and the presence or absence of bleeding on probing. Clinical attachment levels were estimated from amalgam restorations placed in the crowns of all premolar teeth according to the method of Lindhe, J., S-E Hamp, and H. Loe, J. Periodont. Res. 8:1 (1973). Pocket depths were measured at six points around each tooth and extraoral lateral X-rays were taken at day 0 and following the termination of the study.

Blood samples were drawn from the cephalic vein by venipuncture with a syringe. Crevicular fluid was collected in volumetric micropipettes (Drummond Scientific Co. Broomall, PA) positioned extracrevicularly near the margin of the gingiva. Samples visibly contaminated with blood were discarded. Clinical indices (except the plaque index) were recorded after collection of crevicular fluid in order to avoid trauma to the gingivae. Samples were stored at 4° C. for a maximum of 24 hours before assay. Studies verified that enzyme levels were unaffected after storage for this period.

Two μl of crevicular fluid were diluted to a volume of 200 μl with distilled water, mixed and centrifuged in a Beckman microfuge (Beckman Instruments, Inc., Palo Alto, CA) for one minute to remove bacteria and cellular debris. The supernatant was analyzed according to the method of Reitman, O. S. and S. Frankel, Amer. J. Clin. Path. 28:56 (1957), using the Sigma assay (see example 3). Two hundred μl samples of undiluted serum were similarly assayed.

Dental plaque was collected with currets from the gingival margin of ligated premolar teeth and immediately weighed. Samples were diluted to 500 μl with 0.9% saline, sonicated 10 times for 10 seconds (total time 100 sec), centrifuged for 2 min on a Beckman microfuge and assayed for AST activity as described above.

The results obtained showed that crevicular fluid from dogs with gingivitis contained approximately 10-fold higher concentrations of AST (468±164 (SE) SFU/ml) than serum (41±4 SFU/ml). Two to 3 weeks after ligation, marked increased in AST levels in crevicular fluid, but not in serum, were observed in all dogs (mean AST levels in crevicular fluid before ligation=468±164 SFU/ml, 2 weeks post-ligation=3209±1435 SFU/ml). Plaque contained insufficient enzyme (mean=2.75 SFU/mg) to account for the levels found in crevicular fluid collected at the same time from the same sites.

Results are shown in FIGS. 1 and 2, and in Table I and II below.

FIG. 1

FIG. 1 shows the mean levels of AST in serum and crevicular fluid (±SE), and the mean gingival indices and clincial estimations of attachments levels measured at weekly intervals for the duration of the study. Crevicular fluid was frequently unobtainable from pre-ligation sites in sufficient quantities for estimation of AST levels. Therefore pre-ligation values include samples from other quadrants. The mean gingival index data include only the three values recorded from the buccal surfaces of each premolar tooth. (*=The gingival indices from two animals only were recorded at this time.)

Aspartate aminotransferase was markedly elevated in crevicular fluid two weeks after ligation. This increased level was significantly greater than the mean level of AST before ligation (P>0.05). The occurrence of the peak AST level at this time, and not earlier, suggests that it did not result from tissue trauma induced by ligature placement. The peak does coincide with the period of high levels of soft tissue destruction and osteoclast activity reported in the beagle dog by Schroeder, H. E. and J. Lindhe, J. Periodontal. 51:6 (1980) and with the period of active bone resorption in ligature-induced periodontitis in the monkey, reported by Hausmann, E., L. F. Ortman, and N. Sedransk, Calcif. Tissue Int. 29:133 (1979). The results suggest that the initial peaks in AST levels in crevicular fluid represent the acute destructive episodes of active periodontal disease which have been described in this model.

After the initial peak, the mean levels of AST in crevicular fluid were not significantly different from pre-ligation levels. FIG. 1 also illustrates that mean AST levels in crevicular fluid did not correlate with clinical attachment levels or the gingival index. This absence of correlation was also observed when the data from individual dogs were analyzed (data not shown). Schroeder, H. E. and J. Lindhe, J. Periodontol 51:6 (1980) have demonstrated that the initial destruction of the supra-alveolar connective tissue and coronal portions of the alveolar bone in ligature-induced periodontal disease is unrelated to attachment loss as measured by apical migration of the epithelial attachment. The lack of correlation between AST levels in crevicular fluid and gingival inflammation is encouraging because it is important that an assay of disease activity measure a product of tissue destruction and not of gingival inflammation. Although the relationship between inflammation and periodontal tissue destruction is unclear at present, it has been well established that gingival inflammation can exist for long periods without progressing to destructive periodontitis. See Hirshfeld, L. and B. Wasserman, J. Periodontol 49:225 (1978).

FIG. 2

Examination of AST levels in crevicular fluid of individual dogs revealed that all dogs showed increased AST levels subsequent to ligation. Three of the five dogs showed marked increases in AST at 2 weeks after ligation whereas one dog (1315) showed relatively modest AST levels throughout the period of ligation and another dog (1317) showed a peak AST level 13 weeks after ligation. Consistent with the increased levels of AST was the radiographic evidence of increased bone loss around ligated teeth compared to unligated teeth. The pre-ligation and the 2 week post-ligation levels of AST in crevicular fluid of individual dogs are shown in Table I.

The enzyme levels in crevicular fluid of individual dogs revealed variation in individual AST profiles and in the levels from week to week. Several factors may account for this variability. Beagle dogs vary in their susceptibility to naturally occurring periodontitis, indicating a possible variation in host response to periodontophathogenic microorganisms. Moreover, the initiation of destructive periodontitis by subgingival ligature placement is not uniformly predictable and is critically related to the position of the ligature and the presence of ulceration in the pocket epithelium. Furthermore, to maintain the destructive lesion, ligatures must be moved progressively in an apical direction.

TABLE I

Pre-ligation and Peak Post-ligation AST levels in Crevicular Fluid

| | AST Levels (SFU[1]/ml) | |
|---|---|---|
| Dog # | Pre-ligation | 2 Weeks Post-ligation |
| 1312 | * | 4450 |
| 1313 | 0 | 4600 |
| 1315 | 500 | 1754 |
| 1316 | 750 | 4795 |
| 1317 | * | 3421 |

[1]SFU = Sigma-Frankel Unit
*Insufficient crevicular fluid was obtained from these two dogs before ligation for the determination at AST levels.

A possible source of AST in crevicular fluid is dental plaque. Therefore, we examined whether the amount of AST that could be extracted from dental plaque by vigorous sonication could account for the level of AST in crevicular fluid obtained from the same site at the same time. Table II shows that the amount of AST extracted from plaque showed no relationship with the level in crevicular fluid. Samples 5 and 6 which had very low or undetectable levels of AST in plaque and the highest levels of AST in crevicular fluid of the nine samples examined.

TABLE II

AST Levels in Plaque and Crevicular Fluid

| Sample | Wet Weight (mg) | AST Levels Plaque (SFU/mg wet weight) | Crevicular Fluid[1] (SFU/ml) |
| --- | --- | --- | --- |
| 1 | 1.0 | 10 | 438 |
| 2 | 0.7 | 37 | 701 |
| 3 | 0.4 | 28 | 789 |
| 4 | 0.4 | 31 | 526 |
| 5 | 3.6 | 3 | 1053 |
| 6 | 0.5 | 0 | 1404 |
| 7 | 0.7 | 57 | 789 |
| 8 | 0.8 | 13 | 789 |
| 9 | 3.6 | 0 | 526 |
| Mean | 1.3 | 20 | 779 |

[1]Samples obtained immediately before collection of plaque.

Serum AST Levels

In contrast to AST levels in crevicular fluid, no significant change was observed in serum AST levels after ligation. In fact, the AST levels in serum remained relatively unchanged for the duration of the study. This observation strongly suggests that the variations in AST levels in crevicular fluid were not due to systemic factors such as heart or liver damage.

EXAMPLE 13

Determination of Periodontal Disease in Humans

Twelve patients from the University of Illinois Periodontal Clinic (801 S. Paulina, Chicago, IL) were selected on the following bases: 1) they had no history of systemic disease (e.g. cardiac disease, liver disease, etc.); 2) they had received no treatment for periodontal disease for at least one year; and 3) they had taken no systemic medication (e.g. antibiotics) for the previous three months.

Crevicular fluid was collected by capillary tube from 1 site per patient. The sample (1-3 μl) was diluted to 200 μl with distilled water, mixed and centrifuged in a Beckman microfuge (Beckman Instruments, Inc., Palo Alto, CA) for 1 min to remove bacteria and cellular debris. The supernatant was analyzed for AST by the method of Example 3.

In six of the patients, samples of unstimulated mixed saliva were similarly collected and analyzed.

After the crevicular fluid was sampled, each site was evaluated for the presence or absence of gingivitis by the method of Loe, H., and P. Silness, Acta Odont. Scand. 21:533 (1963), and for periodontitis by the method of Ramfjord, S. P., J. Periodontol. 38:602 (1967). Bleeding on probing was also evaluated by the method of Greenstein, A., J. Caton, and A. M. Polson, J. Periodontol. 52:420 (1981).

The results are given in Table III:

TABLE III

| Patient No.[1] | Clinical Impression[2] | Bleeding[3] | Crevicular Fluid Sample Volume (μl) | AST (SFU/ml) |
| --- | --- | --- | --- | --- |
| 1a | P | + | 1 | 375 |
| 1b | P | ± | 1 | 250 |
| 2 | G | + | 3 | 700 |
| 3 | G | + | 1 | 750 |
| 4 | P | + | 1 | 1650 |
| 5 | P |   | 1 | 750 |
| 6 | P | + | 1 | 150 |
| 7 | P | ± | 3 | 757 |
| 8 | P | ± | 1 | 500 |
| 9 | P | ± | 1 | 225 |
| 10 | P | + | 1 | 100 |
| 11a | P | − | 1 | 0 |
| 11b | P | − | 1 | 0 |
| 12a | G | − | 1 | 0 |
| 12b | G | − | 1 | 0 |

[1]In 3 patients (1, 11, and 12) the site was re-evaluated (b) after the initial evaluation (a).
[2]G = gingivitis present according to the method of Loe and Silness. P = periodotitis present according to the method of Ramfjord.
[3](+) = definite bleeding, (±) = minimal bleeding, (−) = no bleeding, according to the method of Greenstein et al.

The mean AST level of crevicular fluid from areas showing no bleeding on probing=0 SFU/ml (N=4), minimal bleeding=464±113 SFU/ml (N=4), and definite bleeding=595±192 SFU/ml (N=6). Comparison of AST levels with clinical impression shows G=363±182 SFU/ml (N=4) and P=424±119 SFU/ml (N=3) respectively. The mean AST level in saliva was 22.1±4.6 SFU/ml (N=6).

These data demonstrate that the subjective clinical impressions traditionally used do not correlate with either bleeding on probing or the objective AST assay, nor do they serve to distinguish active disease from prior damage. High levels of AST correlate with the presence or absence of bleeding on probing but attempts to correlate degree of bleeding with either clinical impressions or relative AST levels fail. Those patients having high AST levels, regardless of clinical impression or degree of bleeding on probing, are predicted to have a high likelihood of progressive disease requiring treatment.

EXAMPLE 14

Microassay Kit

Components (a) 6 endodontic filter points
(b) 7 reaction vessels, labelled 1-7, with caps
(c) Reagent I [0.266 g D,L-aspartic acid and 0.003 g alpha-oxoglutaric acid, in 10 ml phosphate buffer, pH 7.4 containing 2.05 ml 1 N NaOH and a drop of chloroform]
(d) Reagent II ( in brown glass container) [2 mg 2,4-dinitrophenylhydrazine in 10 ml 1 N HCl containing a drop of chloroform]
(e) Reagent III [75 ml 0.4 M NaOH]
(f) 3 disposable 10 ml pipettes
(g) standard color chart showing color intensity at 25° C. vs. AST concentration
(h) directions

[NOTE: The standard practice is to examine each tooth for periodontal disease at six standard points around each tooth. The same six standard points will be used in this assay.]

Directions (1) The kit should be stored refrigerated, preferably at about 4° C.
(2) Before use, the kit must be allowed to warm to room temperature (25° C.).
(3) Set up Tubes 1-7 in sequence.
(4) Sample collection: One of the endodontic filter points provided is touched to the junction of the gum and tooth being assayed at one of the six standard measurement points. This procedure is repeated for each of the standard measurement points. As each sample is collected, it is placed separately in one of Tubes 2-7. (Tube 1 is a control).

(5) Using one of the disposable pipettes provided, add 1 ml Reagent I to each of Tubes 1-7.

(6) Wait 30 minutes.

(7) Using a fresh disposable pipette (provided), add 1 ml Reagent II to each of Tubes 1-7.

(8) Wait 20 minutes.

(9) Using a fresh disposable pipette (provided), add 10 ml Reagent III to each of Tubes 1-7, cap each tube, and mix gently by inversion.

(10) Wait 1 minute.

(11) Compare results with the standard color chart. Tube 1 is a control and should show no color change.

Numerous modifications and variations of the above-described invention are expected to occur to those skilled in the art. In particular, it is expected that modifications of the assay procedures and methods of miniaturization will occur to skilled person; these modifications and minaturizations are comprehended within the scope of this invention. Accordingly, only such limitations as appear in the appended claims should be placed thereto.

I claim:

1. A method for determining the presence of active periodontal disease in the gum of a mammal, comprising:
    a) collecting crevicular fluid from the interface of the gum suspected of having periodontal disease and the adjacent tooth surface;
    b) assaying said crevicular fluid for the level of AST present; and
    c) determining elevation in said AST level relative tot he level of AST normally found in the blood serum of healthy adults of the mammal species being tested.

2. The method of claim 1 wherein said assay is a colorimetric assay.

3. The method of claim 2 wherein said colorimetric assay comprises the steps of:
    (a) collecting a sample of crevicular fluid;
    (b) adding aspartic acid and alpha-oxoglutaric acid to said sample of crevicular fluid;
    (c) adding 2,4-dinitrophenylhydrazine;
    (d) adding alkali; and
    (e) examining the reaction mixture of step (d) for the presence of oxalacetate-2,-4-dinitrophenylhydrazone derivative.

4. The method of claim 3 wherein the collection of crevicular fluid in step (a) is done by means of a capillary tube.

5. The method of claim 3 wherein the collection of crevicular fluid in step (a) is done by means of a syringe.

6. The method of claim 3 wherein the collection of crevicular fluid in step (a) is done by means of an absorbent filter strip.

7. The method of claim 3 wherein the presence of oxalacetate-2,4-dinitrophenylhydrazone derivative is measured in step (e) by means of a spectrophotometer.

8. The method of claim 3 wherein the presence of oxalacetate-2,4-dinitrophenylhydrazone derivative is measured in step (e) by means of a standard color chart.

9. The method of claim 2 wherein said colorimetric assay comprises the steps of:
    (a) collecting a sample of crevicular fluid;
    (b) adding aspartic acid and alpha-oxoglutaric acid to said sample of crevicular fluid;
    (c) adding aniline citrate;
    (d) adding 2,4-dinitrophenylhydrazine;
    (e) adding alkali; and
    (f) examining the reaction mixture of step (e) for the presence of pyruvate-2,-4-dinitrophenylhydrazone derivative.

10. The method of claim 9 wherein the collection of crevicular fluid in step (a) is done by means of a capillary tube.

11. The method of claim 9 wherein the collection of crevicular fluid in step (a) is done by means of a syringe.

12. The method of claim 9 wherein the collection of crevicular fluid in step (a) is done by means of an absorbent filter strip.

13. The method of claim 9 wherein the presence of pyruvate-2,4-dinitrophenylhydrazone derivative is measured in step (e) by means of a spectrophotometer.

14. The method of claim 9 wherein the presence of pyruvate-2,4-dinitrophenylhydrazone derivative is measured in step (e) by means of a standard color chart.

15. The method of claim 2 wherein said colorimetric assay comprises the steps of:
    (a) collecting a sample of crevicular fluid;
    (b) adding aspartic acid, malate dehydrogenase, and NADH to said sample of crevicular fluid;
    (c) adding alpha-oxalacetate; and
    (d) examining the reaction mixture of step (c) for decreasing levels of NADH.

16. The method of claim 15 wherein the collection of crevicular fluid in step (a) is done by means of a capillary tube.

17. The method of claim 15 wherein the collection of crevicular fluid in step (a) is done by means of a syringe.

18. The method of claim 15 wherein the collection of crevicular fluid in step (a) is done by means of an absorbent filter strip.

19. The method of claim 15 wherein the decreasing levels of NADH in step (d) is measured by means of a spectrophotometer.

20. The method of claim 15 wherein the decreasing levels of NADH in step (d) is observed by the unaided eye under ultraviolet light.

21. The method of claim 15, comprising in addition the adding of lactate dehydrogenase in step (b).

22. The method of claim 1 wherein said assay is an immunological assay.

23. The method of claim 22 wherein said immunological assay is a radioimmunoassay.

24. The method of claim 22 wherein said immunological assay is a fluorimetric immunoassay.

25. The method of claim 22 wherein said immunological assay is an enzyme immunoassay.

26. The method of claim 25 wherein said enzyme immunoassay is an enzyme-linked immunosorbent assay.

27. The method of claim 22 wherein said immunological assay comprises the steps of:
    (a) applying a spot of aspartate aminotransferase to an indium-coated glass slide;
    (b) adding to said spot a mixture comprising crevicular fluid and anti-human aspartate aminotransferase antiserum; and
    (c) evaluation the treated spot of step (b) for darkening relative to the untreated spot of step (a).

28. The method of claim 27 wherein said darkening is evaluated in step (c) by means of a densitometer.

29. The method of claim 27, comprising the additional step of adding an antiserum specific for anti-human aspartate aminotransferase antibodies to the treated spot of step (b) before evaluating darkening in step (c).

30. The method of claim 29 wherein said darkening is evaluated in step (c) by means of densitometer.

* * * * *

UNITED STATES PATENT AND TRADEMARK OFFICE
CERTIFICATE OF CORRECTION

PATENT NO. : 5,041,373

DATED : August 20, 1991

INVENTOR(S) : Chambers

It is certified that error appears in the above-identified patent and that said Letters Patent is hereby corrected as shown below:

Column 5, line 55, ")" should be --(--.

Column 7, line 43, after "complex" add --.-- (a period).

Column 7, line 62, after "complex" add --.-- (a period).

Column 8, line 7, after "marker" add --.-- (a period).

Column 8, line 12, "!" should be --,-- (a comma).

Column 8, line 29, after "1-105" insert --;-- (a semi-colon).

Column 8, line 36, after "antibody" add --.-- (a period).

Column 8, line 43, after "labelled" add --.-- (a period).

Column 9, line 23, "moles(s)" should be --mole(s)--.

Column 10, line 1, "miili-International" should be --milli-International--.

Column 10, line 42, "nM" should be --mM--.

Column 10, line 43, after "solution" add --.-- (a period).

Column 11, line 39, after "Reagent" add --.-- (a period).

Column 13, line 37, after "water" add --.-- (a period).

Column 13, l. 53, "cuvet" should be --cuvette--.

Column 14, line 7, after "buffer" insert --.-- (a period).

UNITED STATES PATENT AND TRADEMARK OFFICE
CERTIFICATE OF CORRECTION

PATENT NO. : 5,041,373

DATED : August 20, 1991

INVENTOR(S) : Chambers

It is certified that error appears in the above-identified patent and that said Letters Patent is hereby corrected as shown below:

Column 14, line 63, after "mixture" add --)--.

Column 15, line 8, after "following" add --:-- (a colon).

Column 17, line 3, after "(f)" insert --Buffer B [--.

Column 17, line 42, after "AST" insert --[--.

Column 17, line 45, after "AST" insert --[--.

Column 21, line 21, after "in" delete -- - -- (the hyphen).

Column 21, line 26, "2.75" should be --27.5--.

Column 22, line 56 (footnote), "at" should be --of--.

Column 24, l. 12-12.5 (footnote 2), "periodoti-tis" should be --periodontitis--.

Column 24, line 58, after "assay.]" insert --[1]The endodontic filter points are preferably in a form adapted for use with a standard perioprobe instrument.--.

Column 25, line 20, "person" should be --persons--.

Column 25, line 24, "thereto" should be --thereon--.

UNITED STATES PATENT AND TRADEMARK OFFICE
CERTIFICATE OF CORRECTION

PATENT NO. : 5,041,373

DATED : August 20, 1991

INVENTOR(S) : Chambers

It is certified that error appears in the above-identified patent and that said Letters Patent is hereby corrected as shown below:

Column 25, line 34, "tot" should be --to--.

Column 25, line 35, "he" should be --the--.

Signed and Sealed this

Twenty-ninth Day of November, 1994

Attest:

BRUCE LEHMAN

*Attesting Officer*      *Commissioner of Patents and Trademarks*